United States Patent [19]

Murray et al.

[11] Patent Number: 4,769,328

[45] Date of Patent: * Sep. 6, 1988

[54] EXPRESSION OF BIOLOGICALLY ACTIVE PDGF ANALOGS IN YEAST

[75] Inventors: Mark J. Murray; James D. Kelly, both of King County, Wash.

[73] Assignee: ZymoGenetics Inc., Seattle, Wash.

[*] Notice: The portion of the term of this patent subsequent to Aug. 23, 2005 has been disclaimed.

[21] Appl. No.: 660,496

[22] Filed: Oct. 12, 1984

[51] Int. Cl.⁴ .................... C12P 21/00; C12P 19/34; C12N 15/00; C12N 5/00

[52] U.S. Cl. ...................................... 435/68; 435/70; 435/91; 435/172.3; 435/255; 435/320; 935/13; 935/28; 935/37

[58] Field of Search ............... 435/68, 70, 172.3, 171, 435/235, 241, 244, 317, 320; 935/9, 28, 37, 55, 60

[56] References Cited

U.S. PATENT DOCUMENTS 4,350,687 9/1982 Lipton et al. .

OTHER PUBLICATIONS

Devare et al. (1984) Cell, vol. 36, pp. 43–49.
Robbins et al. (1983) Nature, vol. 305, pp. 605–608.
Kurjan et al. (1982) Cell, vol. 30, pp. 933–943.
Davis et al. (1980) Nature 283, pp. 433–488.
Alber et al. (1982) *Journal of Molecular and Applied Genetics*, vol. 1, pp. 419–434.
Brake, A. et al., Aug. 1984, PNAS 81:4642.
Wang, J. et al., Sep. 1984, J.B.C. 259:10645.
Clarke, M. et al., Mar. 1984, Nature 308:464.
Johnnson, A. et al., May 1984, EMBOJ, 3:921.
Owen, A. et al., Jul. 1984, Science 225:54.
Edens, L. et al., Jun. 1984, Cell 37:629.
Production of Platelet-Derived Growth Factor-Like Molecules and Reduced Expression of Platelet-Derived Growth Factor Receptors Accompany Transformation by a Wide Spectrum of Agents, D. F. Bowen-Pop et al., Proc. Natl. Acad. Sci., vol. 81, Apr. 1984, pp. 2396-2400.
Expression of the PDGF-Related Transforming Protein of Simian Sarcoma Virsu in E. coli, S. G. Devare et al., CELL, vol. 36, pp. 43–49, Jan., 1984.

The C-Sis Gene Encodes a Precursor of the B Chain of Platelet–Derived Growth Factor, A. Johnsson et al., the EMBO Journal, vol. 3, No. 5, pp. 921-928, 1984.
Simian Sarcoma Virus Onc Gene, V-Sis, is Derived from the Gene (or Genes) Encoding a Platelet-Derived Growth Factor, R. F. Doolittle et al., Science, vol. 221, pp. 275-277, Jul. 15, 1983.
Structural and Immunological Similarities Between Simian Sarcoma Virus Gene Product)(s) and Human Platelet-Derived Growth Factor, K. C. Robbins et al., Nature, vol. 305, Oct. 13, 1983, pp. 605-608.
Secretion of Foreign Proteins from Saccharomyces Cerevisiae Directed by Alpha Factor Gene Fusions, C. A. Bitter, et al., Proc. Natl. Acad. Sci. U.S.A., vol. 81, pp. 5330-5334, Sep. 1984.
Expression of a Platelet-Derived Growth Factor-Like Protein in Simian Sarcoma Virus Transformed Cells, T. F. Deuel et al., Science, vol. 221, pp. 1348-1350.
Transforming Potential of Human C-Sis Nucleotide Sequences Encoding Platelet Derived Growth Factor, S. F. Josephs et al., Science, vol. 225, Aug. 10, 1984, pp. 636-639.

(List continued on next page.)

Primary Examiner—Thomas G. Wiseman
Assistant Examiner—Stephan C. Seidman
Attorney, Agent, or Firm—Seed and Berry

[57] ABSTRACT

Biologically active PDGF analogs expressed in yeast are disclosed. The analogs are produced by yeast strains transformed with an extrachromosomal element composed of a strong transcriptional promoter directing the expression of a gene which encodes a protein having substantially the same biological activity as PDGF. Suitable genes include the v-sis gene or a derivative of the v-sis gene of simian sarcoma virus or portions thereof, or the human cDNA gene for PDGF or portions thereof. A secretory signal sequence may be provided upstream of the gene, enabling secretion of the gene product from the yeast host cell. Mitogenic activity is one of the biological activities possessed by these PDGF analogs, making them useful in promoting the growth of mammalian cells.

48 Claims, 10 Drawing Sheets

OTHER PUBLICATIONS

Simian Sarcoma Virus-Transformed Cells Secrete a Mitogen Identical to Platelet-Derived Growth Factor, A. J. Owen et al., Science, vol. 225, Jul. 6, 1984, pp. 54–56.

A V-Sis Oncogene Protein Produced in Bacteria Competes for Platelet-Derived Growth Factor Binding to its Receptor, J. Y. J. Wang et al., Journal of Biological Chemistry, vol. 259, No. 17, 9/10/84, pp. 10645–10648.

Structure of a Yeast Pheromone Gene (MFα): a Putative α-Factor Precursor Contains Four Tandem Copies of Mature α-Factor, J. Kurjan et al., Cell, vol. 30, pp. 933–943, Oct., 1982.

FIG. 1A

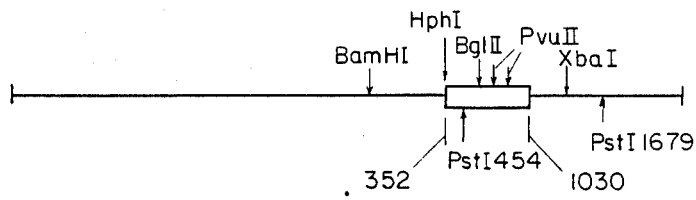

FIG. 1B

```
Hph I                      v-sis-helper viral junction
 |           367            |           382                      397
CT ATG ACC CTC ACC TGG CAG GGG GAC CCC ATT CCT GAG GAG CTC TAT AAG ATG
   MET Thr Leu Thr Trp Gln Gly Asp Pro Ile Pro Glu Glu Leu Tyr Lys MET Pst I
         412                427                442          |   457
CTG AGT GGC CAC TCG ATT CGC TCC TTC AAT GAC CTC CAG CGC CTG CTG CAG GGA
Leu Ser Gly His Ser Ile Arg Ser Phe Asn Asp Leu Gln Arg Leu Leu Gln Gly 472                487                502
GAG TCC GGA AAA GAA GAT GGG GCT GAG CTG GAC CTG AAC ATG ACC CGC TCC CAT
Asp Ser Gly Lys Glu Asp Gly Ala Glu Leu Asp Leu Asn MET Thr Arg Ser His 517             532             547             562
TCT GGT GGC GAG CTG GAG AGC TTG GCT CGT GGG AAA AGG AGC CTG GGT TCC CTG
Ser Gly Gly Glu Leu Glu Ser Leu Ala Arg Gly Lys Arg Ser Leu Gly Ser Leu 577             592             607
AGC GTT GCC GAG CCA GCC ATG ATT GCC GAG TGC AAG ACA CGA ACC GAG GTG TTC
Ser Val Ala Glu Pro Ala MET Ile Ala Glu Cys Lys Thr Arg Thr Glu Val Phe Bgl II
622             637             652             667
GAG ATC TCC CGG CGC CTC ATC GAC CGC ACC AAT GCC AAC TTC CTG GTG TGG CCG
Glu Ile Ser Arg Arg Leu Ile Asp Arg Thr Asn Ala Asn Phe Leu Val Trp Pro
```

```
         682                    697                     712                    727
 CCC TGC GTG GAG GTG CAG CGC TGC TCC GGC TGT TGC AAC AAC CGC AAC GTG CAG
 Pro Cys Val Glu Val Gln Arg Cys Ser Gly Cys Cys Asn Asn Arg Asn Val Gln

|Pvu II
                 742           ↓       757                    772
 TGC CGG CCC ACC CAA GTG CAG CTG CGG CCA GTC CAG GTG AGA AAG ATC GAG ATT
 Cys Arg Pro Thr Gln Val Gln Leu Arg Pro Val Gln Val Arg Lys Ile Glu Ile 787                    802                    817                    832
 GTG CGG AAG AAG CCA ATC TTT AAG AAG GCC ACG GTG ACG CTG GAG GAC CAC CTG
 Val Arg Lys Lys Pro Ile Phe Lys Lys Ala Thr Val Thr Leu Glu Asp His Leu

Pvu II
             847                   862                    877
 GCA TGC AAG TGT GAG ATA GTG GCA GCT GCA CGG GCT GTG ACC CGA AGC CCG GGG
 Ala Cys Lys Cys Glu Ile Val Ala Ala Ala Arg Ala Val Thr Arg Ser Pro Gly 892                    907                    922                    937
 ACT TCC CAG GAG CAG CGA GCC AAA ACG ACC CAA AGT CGG GTG ACC ATC CGG ACG
 Thr Ser Gln Glu Gln Arg Ala Lys Thr Thr Gln Ser Arg Val Thr Ile Arg Thr 952                    967                    982                997
 GTG CGA GTC CGC CGG CCC CCC AAG GGC AAG CAC CGG AAA TGC AAG CAC ACG CAT
 Val Arg Val Arg Arg Pro Pro Lys Gly Lys His Arg Lys Cys Lys His Thr His 1012                   1027                   1043        1053
 GAC AAG ACG GCA CTG AAG GAG ACC CTC GGA GCC TAA GGGCATCGGC AGGAGAATAT
 Asp Lys Thr Ala Leu Lys Glu Thr Leu Gly Ala 1063       1073       1083       1093       1103       1113      1123
 GGGCAGCGGG TCTCCTGCCA GCGGCCTCCA GCATCTTGCC CAGCAGCTCA AGAAGAGAAA AAAGGACTGA 1133       1143       1153       1163       1173       1183      1193
 ACTCCACCAC CATCTTCTTC CCTTAACTCC AAAAACTTGA AATAAGAGTG TGAAAGAGAC TGATAGGGTC 1203       1213       1223       1233       1243       1253      1263
 GCTGTTTGAA AAAAACTGGC TCCTTCCTCT GCACCTGGCC TGGGCCACAC CCAAGTGCTG TGGACTGGCC 1273       1283       1293       1303       1313       1323      1333
 CGAGGGGCCC TGCACGTGGC CCTGAGCACC TCTCAGTGTA GCCTGCCTGG TCCCTAGACC CCTGGCCAGC

XbaI| v-sis-helper viral junction
        1343       1353       1363       1373         ↓↓
 TCCAAGGGGA GGCACCTCCA GGCAGGCCAG CTACCTCGG GGGTCTAG
```

FIG. 1B

EXPRESSION OF BIOLOGICALLY ACTIVE PDGF ANALOGS IN YEAST

TECHNICAL FIELD

The present invention relates to the production of PDGF analogs in general, and more specifically, to the expression of biologically active PDGF analogs in yeast.

BACKGROUND ART

Human platelet derived growth factor (PDGF) has been shown to be the major mitogenic protein in serum for mesenchymal derived cells. This is well documented by numerous studies of platelet extracts or purified PDGF induction of either cell multiplication of DNA synthesis (a prerequisite for cell division) in cultured smooth muscle cells, fibroblasts and glial cells (Ross et al., *PNAS* 71: 1207, 1974; Kohler and Lipton, *Exp. Cell Res.* 87: 297,1947; Estermark and Wasteson, *Exp. Cell Res.* 98: 170, 1976; Heldin et al., *J. Cell Phyiol.* 105: 235, 1980; Raines and Ross, *J. Biol. Chem* 257: 5154, 1982). Furthermore, PDGF is a potent chemoattractant for cells that are responsive to it as a mitogen (Grotendorst et al., *J. Cell Phyiol.* 113: 261, 1982; Seppa et al., *J. Cell Biol.* 92: 584, 1982). It is not generally the case that mitogens also act as chemotactic agents. Due to its mitogenic activity, PDGF is useful as an important component of a defined medium for the growth of mammalian cells in culture, making it a valuable research reagent with multiple applications in the study of animal cell biology.

In vivo, PDGF normally circulates stored in the alpha granules of platelets. Injury to arterial endothelial linings causes platelets to adhere to the exposed connective tissue and release their granules. The released PDGF is thought to chemotactically attract fibroblasts and smooth muscle cells to the site of injury and to induce their focal proliferation as part of the process of wound repair (Ross and Glomset, *N. England Journal of Medicine* 295: 369,1976).

It has been postulated that as a part of this response to injury, PDGF released by platelets may play a causative role in the development of the proliferative lesions of atherosclerosis (Ross and Glomset, ibid.) which is one of the principal causes of myocardial and cerebral infraction. Strategies for the prophylaxis and treatment of atherogenesis in the past have been narrowly directed toward reducing risk factors for the disease, such as lowering blood pressure in hypertensive subjects and reducing elevated cholestrol levels in hypercholesterolemic subjects.

Recent studies have shown that one of the two protein chains comprising PDGF and the putative transforming protein of simian sarcoma virus (SSV), an acute transforming retrovirus, appear to have arisen from the same or closely related cellular genes. In particular, computer analysis of a partial amino acid sequence of PDGF has revealed extensive homology with the gene product, $p28^{sis}$, of SSV (Doolittle, Waterfield and Johnson, ibid.). Further, more recent studies have illustrated that $p28^{sis}$ and PDGF show antigenic as well as structural similarities (Robbins et al., *Nature* 305: 605, 1983; Niman, *Nature* 307: 180, 1984).

Although previous attempts, such as that summarized in Devare et al. (*Cell* 36: 43, 1984), have been made to express the v-sis gene in a transformed microorganism, they have not been successful in producing mitogenic material. More recently, investigators have described the production of $p28^{sis}$ in *E. coli* as a fusion protein. (Wang et al., *J. Biol. Chem* 259: 10645, 1984). This protein appears to compete with PDGF for binding to PDGF receptor sites. While SSV transformed rodent cells have been shown to exhibit a mitogenic activity similar to PDGF (Deuel, et al., *Science* 221:1348, 1983; Own, et al., *Science* 225: 54, 1984), it is not clear that this activity is due to a gene product from SSV (i.e., $p28^{sis}$). Furthermore, cells transformed by a variety of viruses other than SSV produce a PDGF-like mitogen into the culture medium (Bowen-Pope et al., *PNAS* 81: 2396, 1984).

While natural PDGF may be isolated from human plasma or platelets as starting material, it is a complex and expensive process, in part due to the limited availability of the starting material. In addition, it is difficult to purify PDGF with high yield from other serum components due to its extremely low abundance and biochemical properties. Furthermore, the therapeutic use of products derived from human blood carries the risk of disease transmission due to contamination by, for example, hepatitis virus, cytomegalovirus, or the causative agent of Aquired Immune Deficiency Syndrome (AIDS).

In view of PDGF's clinical applicability in the treatment of injuries in which healing requires the proliferation of fibroblasts or smooth muscle cells and its value as an important component of a defined medium for the growth of mammalian cells in culture, the production of useful quantities of protein molecules similar to authentic PDGF which possess mitogenic activity is clearly invaluable.

In addition, the ability to produce relatively large amounts of PDGF would be a useful tool for elucidating the putative role of the v-sis protein, $p28^{sis}$, in the neoplastic process.

Further, since local accumulation of smooth muscle cells in the intamal layer of an arterial wall is central to the development of atherosclerotic lesions (Ross and Glomset, ibid.), one strategy for the prophylaxis and treatment of atherosclerosis would be to suppress smooth muscle cell proliferation. The ability to produce large amounts of PDGF would be useful in developing inhibitors or designing specific approaches which prevent or interfere with the in vivo activity of PDGF in individuals with atherosclerosis.

DISCLOSURE OF THE INVENTION

Briefly stated, the present invention discloses an extrachromosomal element capable of replication in yeast and containing a yeast promoter capable of directing the expression of biologically active PDGF analogs, the yeast promoter being followed downstream by a gene encoding a protein having substantially the same structure and/or mitogenic activity as PDGF. The gene may be the v-sis gene or a derivative of the v-sis gene of simian sarcoma virus or portions thereof, or the human cDNA gene for PDGF or portions thereof. Another aspect of the invention discloses a method of preparing biologically active PDGF analogs by introducing into a yeast host an extrachromosomal element capable of replication in yeast and containing a yeast promoter capable of directing the expression of biologically active PDGF analogs, the yeast promoter being followed downstream by a gene encoding a protein having substantially the same structure and/or mitogenic activity as PDGF, subsequently growing said yeast host in an appropriate medium, and then isolating the protein product of the gene from the culture medium. Yeast cells transformed with such an element are also disclosed.

The present invention further provides a method for promoting the growth of mammalian cells through incubating the cells with a PDGF analog expressed by the yeast host cells transformed with an extrachromosomal element capable of replication in yeast and containing a yeast promoter capable of directing the expression of the biologically active PDGF analogs, the yeast promoter being followed downstream by a gene encoding a protein having substantially the same structure and/or mitogenic activity as PDGF.

Other aspects of the invention will become evident upon reference to the following detailed description and attached drawings.

BRIEF DESCRIPTION OF THE DRAWINGS

FIG. 1A is a schematic restriction map of the proviral genome of SSV.

FIG. 1B depicts the nucleotide sequence and predicted amino acid sequence encoded by the v-sis region of SSV genome.

BEST MODE FOR CARRYING OUT THE INVENTION

Figure 2:
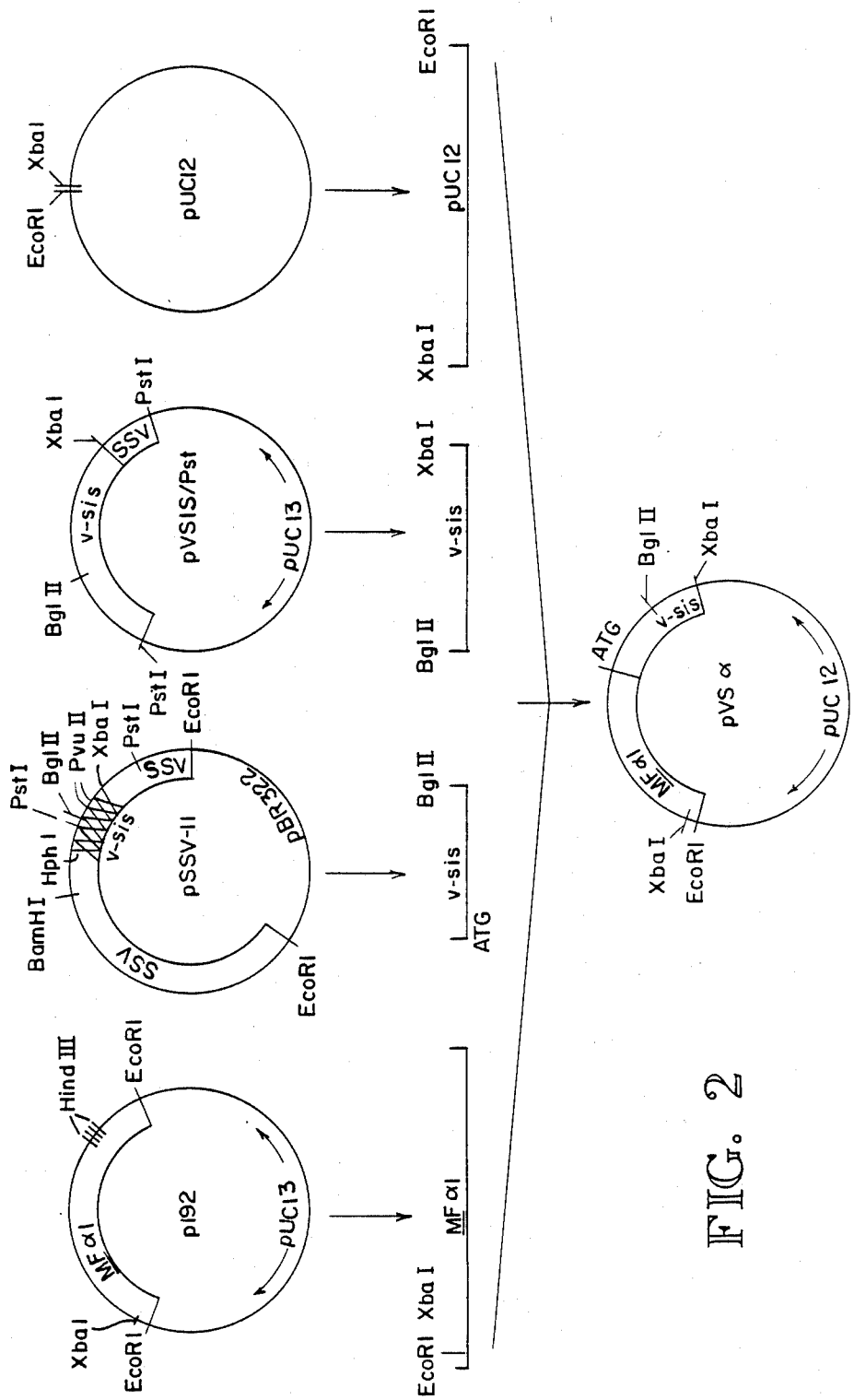
FIG. 2 illustrates the construction of a plasmid which contains the MFα1 promoter and secretory signal sequence upstream of the v-sis gene.

Prior to setting forth the invention, it may be helpful to an understanding thereof to set forth definitions of certain terms to be used hereinafter.

Polypeptides:
A polymer of amino acids.
Reading Frame:
The arrangement of nucleotide codons which encode an uninterrupted stretch of amino acids. During translation of an mRNA the proper reading frame must be maintained. For example, the sequence GCUGGU-UGUAAG may be translated into three reading frames or phases depending on whether one starts with G, with C, or with U, and thus may yield three different peptide products. Translation of the template begins with an AUG codon, continues with codons for specific amino acids, and terminates with one of the translation termination codons.

Coding Sequence:
DNA sequences which in the appropriate reading frame directly code for the amino acids of a protein.
Complementary DNA:
or cDNA. A DNA molecule or sequence which has been enzymatically synthesized from the sequences present in an mRNA template.
Secretory Signal Sequence:
That portion of a gene encoding a signal peptide. A signal peptide is the amino acid sequence in a secretory protein which signals its translocation into the secretory pathway of the cell. Signal peptides generally occur at the beginning (amino terminus) of the protein and are 20-40 amino acids long with a stretch of 9-10 hydrophobic amino acids in their center. Very often the signal sequence is proteolytically cleaved from the protein during the process of secretion.
Cell Surface Receptor:
A protein molecule at the surface of a cell which specifically interacts with or binds a molecule approaching the cell's surface. Once the receptor has bound the cognate molecule, it effects specific changes in the physiology of the cell.
Mitogen:
A molecule which stimulates cells to undergo mitosis. Mitosis is asexual somatic cell division leading to two daughter cells, each having the same number of chromosomes as the parent cell.
Transformation:
The process of stably and hereditably altering the genotype of a recipient cell or microorganism by the introduction of purified DNA. This is typically detected by a change in the phenotype of the recipient organism.
Transcription:
The process of producing mRNA template from a structural gene.
Expression:
The process, starting with a structural gene, of producing its polypeptide, being a combination of transcription and translation. An expression vector is a plasmid derived construction designed to enable the expression of a gene carried on the vector.
Plasmid:
An extrachromosomal double stranded DNA sequence comprising an intact "replicon" such that the plasmid is replicated in a host cell. When the plasmid is placed within a unicellular organism, the characteristics of that organism may be changed or transformed as a result of the expression of the DNA sequences of the plasmid. For example, a plasmid carrying the gene for tetracycline resistance (tet$^R$) transforms a cell previously sensitive to tetracycline into one which is resistant to it.
Yeast Promoter:
DNA sequences upstream from a yeast gene which promotes its transcription.
Biological Activity:
Some function or set of activities performed by a molecule in a biological context (i.e., in an organism or an in vitro facsimile). In the case of PDGF, these biological activities include binding to cell surface receptor molecules, inducing chemotaxis and inducing mitogenesis of responsive cell types.

As noted above, human platelet derived growth factor (PDGF) has been shown to be a major mitogenic protein in serum. PDGF is known to be composed of two polypeptide chains, an A chain and a B chain, which are held together by disulfide bonds to form the biologically active molecule. The A chain and B chain alone do not appear to exhibit any mitogenic activity, (Raines and Ross, ibid.) and attempts to reconstitute activity by reoxidation of the reduced polypeptides have not been successful. Recently, the amino acid sequence of the B chain has been shown to be substantially homologous to a portion of the v-sis gene product, p28$^{sis}$ (Doolittle et al. *Science* 221: 275, 1983; Waterfield et al. *Nature* 304: 35, 1984; and Johnson et al. *Embo* 3: 921, 1984). The homology between these two proteins strongly suggests that they are derived from the same or closely related cellular genes.

Given the fact that the B chain alone is not biologically active and that previous attempts directed toward expressing v-sis sequences in *E. coli* did not yield mitogenic material, it would not be expected that merely expressing a portion of the v-sis gene homologous to a portion of the PDGF gene in a microorganism would result in a molecule which exhibited mitogenic activity. The present invention however, unlike the previous attempts noted above, was designed to express the v-sis gene or portions thereof absent of heterologous sequences, such that the expressed molecules are more closely related to the B chain of PDGF. Further, the expression system of the present invention was designed to produce the gene product via a eucaryotic secretory pathway. This enables the expressed protein molecules to be properly processed and assembled such that they exhibit biological activity. Indeed, the present invention, in contrast to previous efforts, results in the secretion of PDGF analogs which are biologically active.

In its active form, PDGF is a heat stable protein composed of heterogeneously sized species of between 28,000 and 31,000 Daltons, all of the individual species being active in and stimulating DNA synthesis (Raines and Ross, ibid.; Deuel et al., *J. Biol. Chem.* 256: 8896, 1981; Antoniades, PNAS 78: 1981). Where individual species withmolecular weights of 27,000; 28,500; 29,000; and 31,000 Daltons have been isolated and assayed, they have been found to have comparable mitogenic activity and amino acid composition (Raines and Ross, ibid.) Further, these species show extensive tryptic peptide homology. The slight variations in size among the species are most probably due to differences in carbohydrate composition and proteolysis.

Through studies of PDGF which has been extensively purified from platelet-rich human plasma, it is likely, as noted above, that PDGF is composed of two polypeptide chains, an A chain (14,000 Daltons) and a B chain (16,000 Daltons), which are disulfide bonded together to form the biologically active dimer molecule (Raines & Ross, Deuel et al., Antoniades, ibid.). The PDGF nomenclature found in the literature is not consistent (Doolittle et al., Waterfield et al., Raines and Ross, Johnson et al. ibid.). The nomenclature of Johnsson et al. (ibid.) wherein the two polypeptides found in pure PDGF are called A chain and B chain. The B chain is homologous to p28$^{sis}$ and was previously called "peptide I" (Waterfield et al., ibid.) or "1a" (Doolittle et al., ibid.). The A chain was previously termed "peptide II" (Waterfield et al., ibid.) or "2a" (Doolittle et al., ibid.). Data derived from a partial amino acid sequence of PDGF indicate that the two polypeptide chains (A chain and B chain) show some homology (Doolittle et al., ibid., Waterfield et al., ibid., and Johnsson et al., ibid., Antoniades and Hunkapiller *Science* 220: 963, 1983). The A chain and B chain alone do not appear to exhibit any mitogenic activity, and attempts to reconstitute activity by reoxidation of the reduced polypeptides have not been successful (Raines & Ross, ibid.).

The v-sis gene, as mentioned above, is the transforming gene of simian sarcoma virus (SSV). The v-sis gene has been cloned and its DNA sequence determined (Devare et al., *PNAS* 79: 3179, 1982; Devare et al., *PNAS* 80: 731, 1983). Analysis of this sequence revealed an open reading frame which could encode a 28,000 Dalton protein, designated p28$^{sis}$. Subsequently, such a protein was identified in SSV infected cells (Niman, ibid.; Robbins, ibid.). The predicted amino acid sequence of the v-sis gene product, p28$^{sis}$, was found to have a high degree of homology with the actual amino acid sequence of a portion of the B chain of PDGF (Johnsson, ibid.). The homology of the PDGF B chain to the v-sis gene product begins at amino acid 67 of p28$^{sis}$, a serine, and continues for approximately 109 amino acids to a threonine residue at amino acid 175. The amino acid sequences preceding and following the B chain homologous region of p28$^{sis}$ are not homologous to either the A or B chains of mature PDGF (Johnsson, ibid.) In addition, PDGF and p28$^{sis}$ have been shown to be similar antigenically (Niman, ibid.; Robbins, ibid.). The v-sis gene product, p28$^{sis}$, a protein of approximately 225 amino acids, appears to be proteolytically processed to a protein of approximately 20,000 Daltons (p20$^{sis}$) in SSV infected cells (Niman, ibid.; Robbins, ibid.). This 20,000 Dalton protein can be immunoprecipitated with antiserum against PDGF.

In the present invention, the v-sis gene and a fragment thereof containing the 109 amino acids with homology to the PDGF B chain were inserted into yeast extrachromosomal elements containing a yeast promoter capable of directing the expression of biologically active PDGF analogs. In accordance with the present invention, the yeast promoter is followed downstream by a fragment of the v-sis gene which encodes a protein having substantially the same structure and/or mitogenic activity as PDGF.

Genes which encode a protein having substantially the same structure and/or mitogenic activity as PDGF include the v-sis gene or a derivative of the v-sis gene of simian sarcoma virus (SSV) or portions thereof or the human cDNA gene for PDGF or portions thereof. The genes to be utilized in the extrachromosomal element may be isolated using standard recombinant DNA techniques.

The human PDGF cDNA gene may be isolated from a human cDNA library made from an appropriate source of messenger RNA by using the v-sis gene or a fragment thereof as a hybridization probe. A preferred source of mRNA is human umbilical vein endothelial cells. These cells can be cultured in vitro for short periods of time and are known to secrete PDGF into the culture medium (DiCorleto and Bowen-Pope, *PNAS* 80: 1919, 1983). The identity of this cDNA gene as that encoding PDGF may be verified by DNA sequencing.

Promoters which may be utilized in this context include the yeast alpha-factor (MFα1) promoter and the yeast triose phosphate isomerase (TPI) promoter. Promoters may also be obtained from other yeast genes, e.g. Alcohol Dehydrogenase 1 (ADH1), Alcohol Dehydrogenase 2 (ADH2).

The constructions described herein were designed such that the v-sis gene product would be secreted from the yeast cell into the media. This was accomplished through use of the secretion signal sequence of the yeast mating pheromone alpha-factor (Kurjan and Herskowitz, *Cell* 30: 933, 1982; Julius et al., *Cell* 36: 309, 1984; and Brake et al., *PNAS* 81: 4642, 1984) although other secretion signals may be used. To ensure the efficient transcription termination and polyadenylation of mRNA, a yeast terminator sequence, such as the triose phosphate isomerase terminator, was added. (Alber and Kawasaki, *J. Molec. Genet. Appl.* 1: 419, 1982).

Once an appropriate DNA fragment containing the gene of interest is identified, it is ligated to an appropriate promoter and secretory signal fragment. Methods of ligation of DNA fragments have been amply described (Maniatis et al., *Molecular Cloning: A Laboratory Manual*, Cold Spring Harbor Laboratory 1982) and are well within the skill of those of ordinary skill in the art to perform. After preparation of the v-sis expression constructions, the constructs are inserted into a yeast expression vector.

The replicating plasmid YEp13, containing an origin of replication and a selectable marker, the LEU2 gene, was used for the initial expression constructions. The use of the selectable marker LEU2 in yeast cells deficient in their ability to synthesize leucine allows for the positive selection of those cells containing the LEU2 plasmid by their ability to grow on minus leucine growth media. Although these constructions directed the expression of a product having some mitogenic activity, it is preferable to use an expression vector which is more stably maintained within the host cell in order to produce more mitogenic activity per culture.

A suitable expression vector in this regard is the plasmid pCPOT, which includes the *Schizosaccharomyces pombe* gene encoding the glycolytic enzyme triose phosphate isomerase (POT1 gene). Inclusion of the POT1 gene ensures the stable maintenance of the plasmid in an appropriate host cell due to its ability to complement the corresponding gene deletion present within this host cell. In addition, the MFα1 promoter was replaced by the *Saccharomyces cerevisiae* TPI promoter with the intention of further increasing transcription and expression.

After preparation of the DNA construct incorporating the TPI promoter, the alpha factor signal secretory signal sequences, the appropriate segment of the v-sis gene or the human cDNA gene for PDGF, and the TPI terminator in an appropriate vector, the construct is transformed into the yeast host with a TPI deletion. Procedures for transforming yeast are well known in the literature.

The transformed yeast cells may be selected for by growth on conventional complex medium containing glucose when the pCPOT vector is utilized. A conventional medium such as YEPD (20 grams glucose, 20 grams Bacto-peptone, 10 grams yeast extract per liter) may be used. Once selected, transformants containing the v-sis expression constructions are grown to stationary phase on conventional complex media, the cells removed, and the medium concentrated. Noting that authentic human PDGF is a highly cationic and hydrophobic protein (Raines and Ross ibid., Antoniades ibid., Deuel et al., 1981, ibid.), it was expected that the putative yeast product would possess similar characteristics, allowing it to be concentrated on a hydrophobic chromatography matrix such as C8-Sepharose (Pharmacia Fine Chemicals AB, Uppsala, Sweden).

Using a variety of assays, it is demonstrated that growth media from yeast cultures expressing the v-sis derivatives possess biological activities identical to authentic human PDGF.

The techniques of cell culture have advanced considerably in the last several years as have the number and varieties of mammalian cells which will grow in culture. Central to these advances is a better understanding of the nutritional requirements (i.e., hormones and growth factors) of cultured cells (Barnes and Sato, *Cell* 22: 649, 1980). The types of cells able to grow in culture can be crudely classified in two groups: normal and transformed. So-called normal cells are generally not immortal in culture, they do not form tumors when injected into animals and they retain a normal diploid karyotype. Normal cells may also retain much of their differentiated character in culture. Within the category of normal cells are those which will only grow for a limited number of generations in culture, termed cell strains or primary cultures. Some normal cell lines, while not meeting all the criteria of transformation, may grow indefinitely in culture. Transformed cells are immortalized for growth in culture, typically have lost their differentiated phenotype and have acquired karyotypic aberrations. They may also be independent of anchorage for growth and induce tumors when injected into the appropriate host animal. Cells in any of these categories which grow in vitro and possess PDGF receptors will be responsive to the PDGF analogs of this invention in culture.

To summarize the examples which follow, Example I demonstrates the construction of a v-sis subclone of pSSV-11 in the *E. coli* replicating plasmid pUC13, subsequently designated pVSIS/Pst. Example II demonstrates the construction of the plasmid pVSα, which includes the ligation of v-sis to the MFα1 promoter and secretory signal sequence. EXAMPLE III demonstrates the oligonucleotide directed deletion mutagenesis of the first 195 base pairs of the v-sis gene using a technique which employs single stranded bacteriophage M13, in order to eliminate the first sixty-six amino acids of the v-sis gene product, p28$^{sis}$, which are not homologous to the B chain of PDGF. A resulting phage with the correct deletion was designated m11vs2α. EXAMPLE IV demonstrates the incorporation of the v-sis related constructions described in Examples II and III into the yeast replicating vector YEp13 and addition of yeast TPI terminator sequences. Subsequently, VS2α sequences were inserted into the plasmid pCPOT, which ensures the stable maintenance of the plasmid in the host cell. This plasmid was designated p117-2. EXAMPLE V demonstrates the transformation of yeast host cells with the plasmids YEpVSα, YEpVS2α, p117-2 and control plasmids p270 and pCPOT, and subsequent transcriptional analysis. EXAMPLE VI demonstrates the concentration of the spent yeast growth media from cultures containing the v-sis expressing transformants and their subsequent analysis for PDGF-like material by the ELISA, radioreceptor and mitogenesis assays. Clear evidence is presented that these yeast media containing the v-sis related gene products described herein possess biological activities identical to authentic human PDGF.

The following examples are offered by way of illustration, and not by way of limitation.

EXAMPLES

Unless otherwise indicated, standard molecular biological methods were used. Restriction endonucleases and other DNA modification enzymes (i.e., T4 polynucleotide kinase, calf alkaline phosphatase, Klenow DNA polymerase) were obtained from Bethesda Research Laboratories, New England Biolabs, Boehringer-Mannhiem or Collaborative Research and were used as the manufacturer suggested unless indicated otherwise. M13 phage and pUC plasmid vectors and appropriate host strains were obtained from Bethesda Research Laboratories. *E. coli* cultures were transformed by the calcium chloride method of Dagert and Ehrlich (*Gene* 6: 23, 1979). Yeast cultures were transformed as described by Beggs (*Nature* 275: 104, 1978). Plasmid and M13 replicative form (RF) DNA were prepared from *E. coli* transformants by the method of Birnboim and Daly (*Nucleic Acids Research* 7: 1513, 1979). Single stranded M13 phage DNA was prepared as described by S. Anderson (*Nucleic Acids Research* 13: 3015, 1981). DNA fragments were extracted from agarose gels by the method of J. Langridge et al. (*Analyt. Biochem.* 103: 264, 1980). DNA sequencing was performed by the dideoxy method on M13 templates (Messing, *Meth. in Enzymology* 101: 20, 1983).

EXAMPLE I

Subcloning of V-SIS from pSSV-11

The SSV retroviral genome was cloned from SSV-11 nonproductively infected normal rat kidney (NRK) cells which had SSV integrated into their genome (Devare et al., 1982, ibid.). The SSV DNA was isolated as a 5.8 kilobase (kb) Eco RI fragment and subsequently inserted into the plasmid pBR322, resulting in the clone pSSV-11. This clone was obtained from S. Aaronson (National Institutes of Health, Bethesda, MD).

FIG. 1A is a schematic restriction map of the 5.8 kilobase proviral genome of SSV. Only the restriction sites relevant to the present invention are indicated. The open box designates the p28$^{sis}$ coding portion of the v-sis gene.

FIG. 1B depicts the nucleotide sequence of the v-sis gene and some flanking SSV sequences. The v-sis gene is inserted 19 nucleotides 3' of the putative ATG initiation codon of the envelope (env) gene of SSV (Devare, et al., 1982, ibid.). It is believed that transcription and translation of v-sis sequences are directed by SSV sequences resulting in an env-sis fusion protein. The nucleotide sequence shown in FIG. 1B is corrected from that published by Devare, et al., in 1982 (ibid.). The corrections include those made by Devare, et al., in 1983 (ibid.) and by the inventors herein. The original numbering scheme of Devare, et al., (1982 ibid.) is retained here for ease of reference. The numbers assigned to the restriction sites in FIG. 1A are from FIG. 1B.

A subclone of pSSV-11 (FIG. 2) containing a portion of the v-sis gene was constructed in the *E. coli* replicating plasmid pUC13 (Vieira and Messing, *Gene*, 19: 259, 1982 and Messing, *Meth. in Enzymology* 101: 20, 1983). Five micrograms (ug) of pSSV-11 was digested with the restriction endonuclease Pst I and the 1.2 kb fragment containing sequences numbered 454–1679 (FIG. 1) was purified by agarose gel electrophoresis (0.9%) and extracted from the gel with cetyltrimethylammonium bromide (CTAB) plus butanol (Langridge et al., ibid.). Two ug of pUC13 was also digested with Pst I, phenol/chloroform (CHCl$_3$) extracted and ethanol (EtOH) precipitated. Forty ng of the 1.2 kb v-sis fragment and 50 ng of Pst I cut pUC13 were ligated overnight at room temperature with 40 units (u) of T$_4$ DNA ligase. The ligation mixture was used to transform *E. coli* K-12 strain JM83 (Messing, Recombinant DNA Technical Bulletin, NIH Publication No. 79-009, 2, No. 2, 43–48, 1979) in the presence of 5-bromo, 4-chloro, 3-indolyl-B-D-galactoside (X-gal) and isopropyl B-D-thiogalactoside (IPTG). Plasmid DNA prepared from ampicillin resistant white colonies was digested with Pst I to verify the presence of the insert and the resulting plasmid was designated pVSIS/Pst.

EXAMPLE II

Construction of the Plasmid pVSα

A. Preparation of V-SIS for Fusion to MFα1

Six hundred ug of plasmid pSSV-11 (FIG. 2) was digested with restriction endonucleases Bam HI and Pvu II in 200 microliters (ul) of 50 mM NaCl, 10 mM MgCl$_2$, 10 mM Tris pH 7.5 (medium salt buffer), and 100 ug/ml bovine serum albumin (BSA), overnight at 37° C. The digestion products were electrophoresed through a 1.1% agarose gel and the 1100 base pair (bp) Bam HI-Pvu II fragment (FIG. 2) cut out, extracted and EtOH precipitated. The DNA pellet was dissolved in 75 ul Hph I buffer to which was added 20 ul of 1 mg/ml BSA and 5 ul Hph I. After overnight digestion at 37° C. the mixture was electrophoresed through a 1.25% agarose gel and the 396 bp Hph I-Pvu II fragment isolated from the gel and EtOH precipitated. The DNA pellet was dissolved in 30 ul of Klenow buffer (6 mM Tris pH 7.5, 6 mM MgCl$_2$, 60 mM NaCl) and the 3' overhanging nucleotide at the Hph I cleavage site removed by treatment with 5 u of Klenow polymerase for 5 minutes at 37° C. One ul of a mixture containing all four deoxyribonucleotides each at 1 mM was added and the reaction mixture incubated an additional 10 minutes. After phenol/CHCl$_3$/ether (Et$_2$O) extraction and EtOH precipitation, the DNA pellet was dissolved in 30 ul of medium salt buffer and digested with 5 u of Bgl II for three hours at 37° C. The DNA was electrophoresed through a 1.25% agarose gel and the 269 bp Hph I-Bgl II fragment extracted and EtOH precipitated. The Hph I cleavage terminus of this Klenow blunted fragment begins with the trinucleotide sequence

5'ATG ... (FIG. 2)
3'TAC ...

B. MFα1 Promoter and Secretory Leader Fragment

Figure 3:
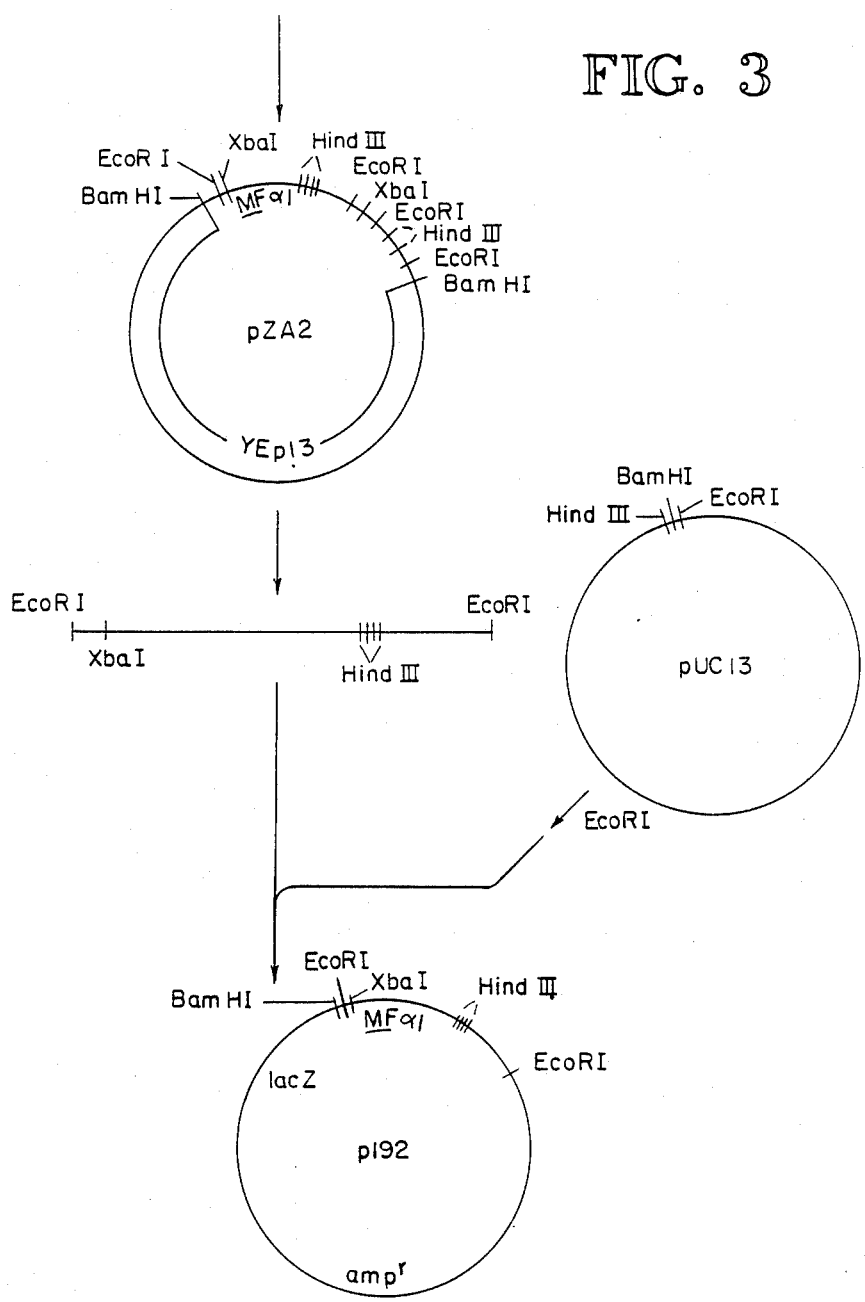
FIG. 3 illustrates the construction of plasmid p192.

Plasmid p192 (FIG. 3) comprises a portion of the gene for the yeast mating pheromone α-factor (MFα1 gene) cloned in the bacterial plasmid pUC13 (Vieira and Messing, ibid. and Messing, *Meth. in Enzymology* 101: 20, 1983). Cloning of the MFα1 gene from a genomic library has been described by Kurjan and Herskowitz (ibid.). The gene was isolated in this laboratory in a similar manner, using as starting material a yeast genomic library of partial Sau 3A fragments cloned into the Bam HI site of Yep13 (Nasmyth and Tatchell, *Cell* 19: 753 1980). From this library, a plasmid was isolated which expressed α-factor in a diploid strain of yeast homozygous for the mat α2-34 mutuation (Manney et al., *J. Cell Biol* 96: 1592, 1983). The clone contained an insert overlapping with the MFα1 gene characterized by Kurjan and Herskowitz (ibid). This plasmid, known as pZA2 (FIG. 3), was cut with Eco RI and the 1700 bp fragment comprising the MFα1 gene was purified. This fragment was then subcloned into the Eco RI site of pUC13 to produce the plasmid p192.

Fifteen ug of plasmid p192 was digested in 30 ul of medium salt buffer with 20 units of Hind III overnight at 37° C. The reaction mixture was diluted to 60 ul with Klenow buffer and the four deoxyribonucleotides added to a final concentration of 50 uM each. Ten units of Klenow polymerase were added to the ice-cold mixture and incubation allowed to proceed 12 minutes at 15° C. Following phenol/ChCl$_3$/Et$_2$O extraction, the aqueous phase was concentrated by lyophilization to a volume of 10 ul and digested with 20 units of Eco RI for 70 minutes at 37° C. The products were electrophoresed through a 0.9% agarose gel and the 1.2 kb Eco RI-Hind III (blunted) MFα1 fragment extracted and EtOH precipitated. This DNA fragment contains the transciptional promoter and secretory signal sequences of MFα1.

C. Preparation of v-sis 3' Sequences and Cloning Vector pUC12; Fragment Ligation Twenty ug of plasmid pVSIS/Pst was digested with Bgl II and Xba I in 40 ul of medium salt buffer. Subsequent electrophoresis through 1% agarose, extraction of the DNA and EtOH precipitation provided the purified v-sis 756 bp Bgl II-Xba I fragment (FIG. 2). *E. coli* replicating plasmid pUC12 (5 ug) was digested with Eco RI and Xba I and gel purified as above (FIG. 2).

Referring to FIG. 2, equimolar amounts of the four DNA fragments described above, adjusted to 10 ng of the 296 bp Hph I-Bgl II v-sis fragment, were mixed in 15 ul of ligase buffer (6 mM Tris pH 7.6, 6.6 mM MgCl$_2$, 0.4 mM ATP, 2 mM spermidine, 20 mM DTT, and 100 ug/ml BSA) and ligated with 40 units of T$_4$ DNA ligase overnight at 14° C. The reaction mixture was brought to room temperature, an additional 150 units of T$_4$ ligase added, and incubated 10 more hours. Seven ul of the ligation mix was used to transform *E. coli* K-12 RR1 (ATCC #31343; Bolivar, E. et al., *Gene* 2: 95 1977), and ampicillin resistant transformants selected. Plasmid DNA was prepared from 12 such bacterial colonies and digested with Xba I. Two clones gave a ~2.2 kb band predicted by the proper fragment alignment (FIG. 2). Further analysis of these by Bgl II-Xba I restriction mapping gave expected bands of approximately 1.5 kb from the MFα1/v-sis fusion and 760bp for the Bgl II-Xba I v-sis fragment. DNA sequence analysis verified the desired nucleotide sequence at the MFα1/v-sis junction. The resultant plasmid was designated pVSα.

EXAMPLE III

Oligonucleotide Directed Deletion Mutagenesis of 66 Amino Terminal v-sis codons

Homology between the v-sis protein p28$^{sis}$, and PDGF begins at amino acid 67 of p28$^{sis}$, a serine residue corresponding to the NH$_2$ terminal residue of the PDGF B chain (Johnsson, ibid.)

Proteolytic processing of the MFα1 primary translation product occurs at the Lys-Arg cleavage signal 85 amino acids from the initiator methionine (Kurjan and Herskowitz, ibid.). A v-sis derivative was constructed in which the first 66 codons of p28$^{sis}$ were removed such that serine residue 67 of v-sis immediately follows the MF 1 Lys-Arg processing signal.

Figure 4:
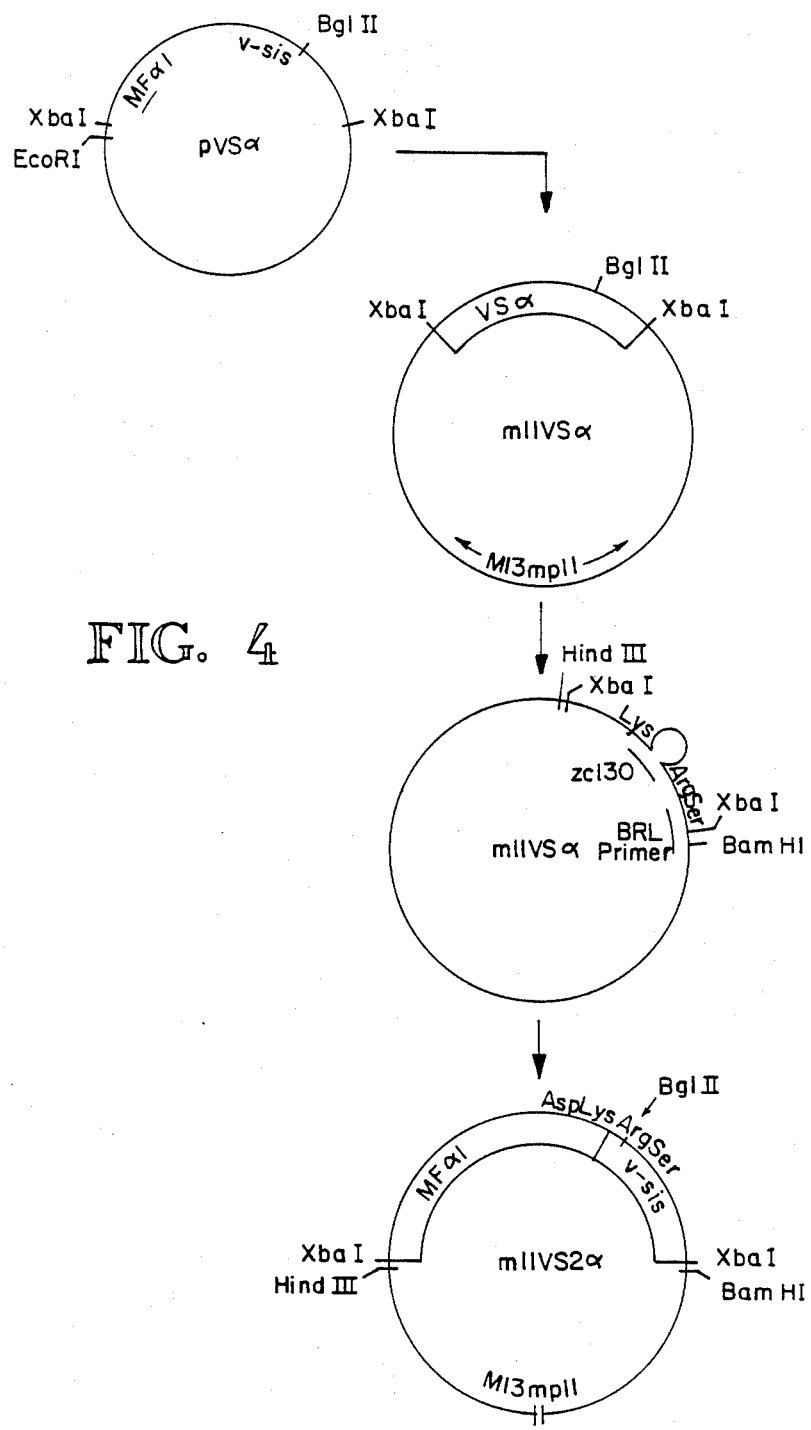
FIG. 4 illustrates the oligonucleotide directed deletion mutagenesis of the amino terminal sixty-six v-sis codons.

Referring to FIG. 4, approximately 40 ng of the gel purified 2.2 kb Xba I fragment of pVSα was ligated with 120 ng of Xba I digested, alkaline phosphatase treated M13mp11 DNA (Messing, *Meth. in Enzymology*, ibid.). The ligation mixture was used to transform *E. coli* K-12 strain JM101 (ATCC 33876) in the presence of X-gal and IPTG. Isolated white plaques were picked and used to infect 3 ml cultures of log phase growth JM101 cells. Replicative Form (RF) DNA was prepared and clones identified which carried the insert fragment in the same orientation as the positive (+) strand form of the single stranded mature phage. Single stranded phage DNA was prepared from one such clone and designated m11VSα.

To precisely remove codons 1-66 of v-sis, oligonucleotide directed mutagenesis was performed essentially according to the two primer method of Zoller (Zoller, et al., *Manual for Advanced Techniques in Molecular Cloning Course*, Cold Spring Harbor Laboratory, 1983). Oligonucleotide ZC 130 3' AGAAACC-TATTTTCCTCGGACCCA 5' was synthesized on an Applied Biosystems 380-A DNA synthesizer. Fifty pmoles of ZC 130 were kinased in 10 ul of kinase buffer (BRL) with 4 units of T$_4$ polynucleotide kinase for 45 minutes at 37° C. The enzyme was inactivated by heating at 65° C. for 10 minutes.

One half pmole of ml1VSα was annealed with 1 pmole of kinased ZC 130 and 1.5 pmoles of universal sequencing primary (BRL) using conditions described (Zoller, ibid.), except that the annealing mixture was first heated to 65° C. for 10 minutes, shifted to 37° C. for 10 minutes, and then quickly chilled on ice. The annealed mixture was then treated with Klenow polymerase as described by Zoller (ibid.) to create circular duplex DNA. Portions of the elongation mixture were used to transform *E. coli* K12 JM 101 cells. The resulting phage plaques were screened for the proper deletion by transfer onto nitrocellulose filters and subsequent hybridization with $^{32}$P phosphorylated ZC 130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and RF DNA was prepared for restriction enzyme analysis. Five isolates showed the expected decrease in size of 195 bp to the 1450 bp Hind III-Bgl II fragment (FIG. 4). DNA sequence analysis of two isolates confirmed the correct fusion junction had been made, thus maintaining the proper translational reading frame. One of these phage was designated M11VS2α.

EXAMPLE IV

Yeast Expression Vectors

A. Construction of Plasmids YEpVSα and YEPVS2α

Yeast Replicating Vector YEp13 (Broach, et al., *Gene* 8: 121, 1979) was used as an expression vehicle for v-sis derived constructions described in Examples II and III. YEp13 is a multicopy extrachromosomal plasmid containing a 2 micron replication origin and the yeast LEU2 gene. This allows for selection of the plasmid in yeast strains possessing a defective chromosomal LEU2 gene when grown on synthetic medium lacking leucine. Addition of yeast terminator sequences to foreign genes expressed in yeast ensures efficient transcription termination and polyadenylation of mRNA. The v-sis expression units VSα and VS2α were placed adjacent to the TPI terminator fragment which was previously cloned into YEp13 (below).

Figure 5:
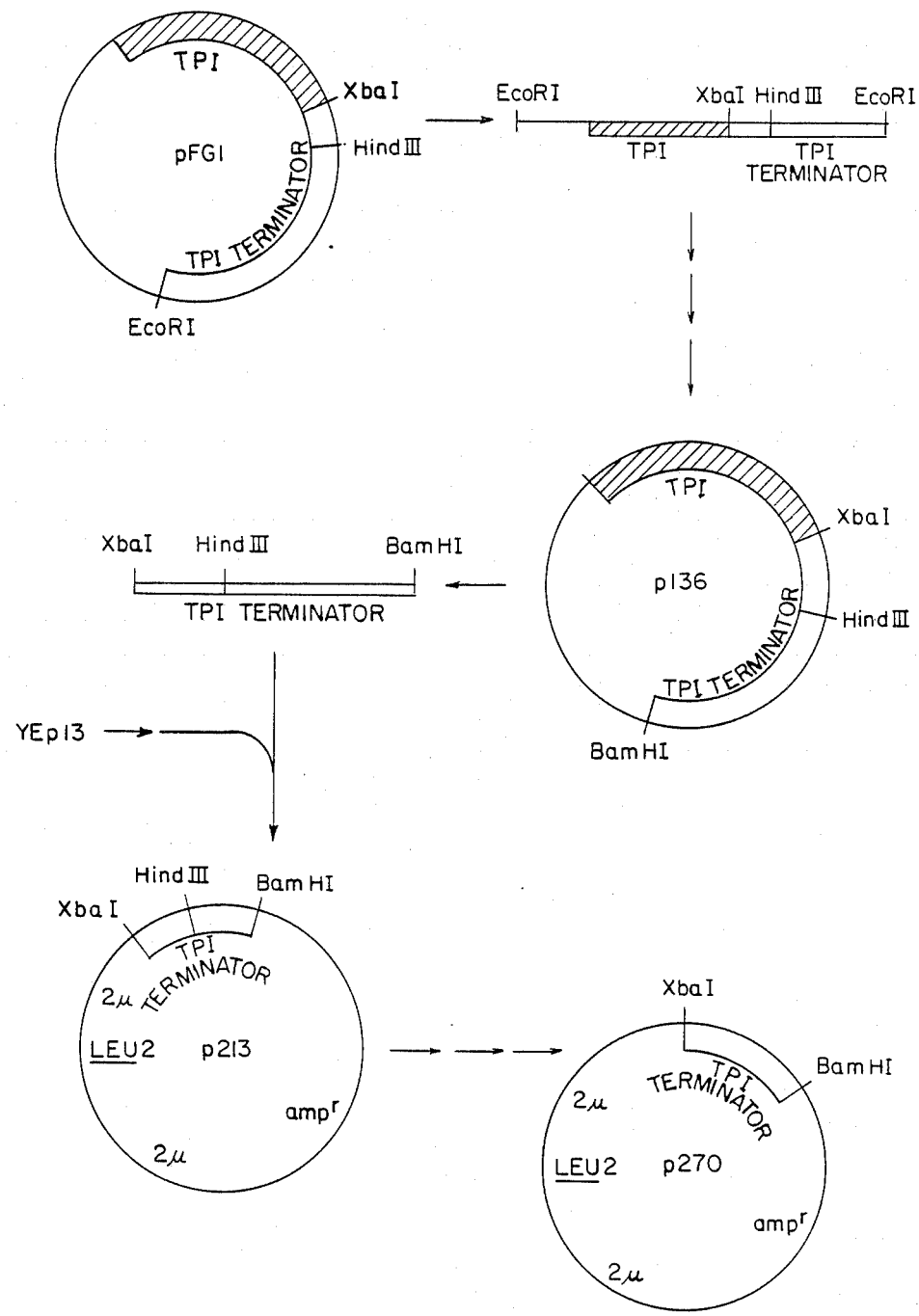
FIG. 5 illustrates the construction of plasmid p270.

Plasmid p270 (see FIG. 5) contains the transcription terminator region of the yeast triose phosphate isomerase (TPI) gene. It was constructed in the following manner. The yeast TPI terminator fragment was obtained from plasmid pFG1 (Albert and Kawasaki, ibid.). It encompasses the region from the penultimate amino acid codon of the TPI gene to the Eco RI site approximately 700 base pairs downstream. A Bam HI site was substituted for this unique Eco RI site of pFGI by first cutting the plasmid with Eco RI, then blunting the ends with DNA polymerase I (Klenow fragment), adding synthetic Bam HI linkers (CGGATCCA), and re-ligating to produce plasmid p136. The TPI terminator was then excised from p136 as a Xba I-Bam HI fragment. This fragment was ligated into YEp13 (Broach, et al., idid.) which had been linearized with Xba I and Bam HI. The resulting plasmid is known as p213. The Hind III site was then removed from the TPI terminator region of p213 by digesting the plasmid with Hind III, blunting the resultant termini with DNA polymerase I (Klenow fragment), and recircularizing the linear molecule using $T_4$ DNA ligase. The resulting plasmid is p270.

Alternatively, p270 may be constructed by digesting plasmid pM220 (see below) with Xba I and Bam HI, purifying the TPI terminator fragment (~700bp) and inserting this fragment into XbaI and Bam HI digested YEp13.

Figure 6:
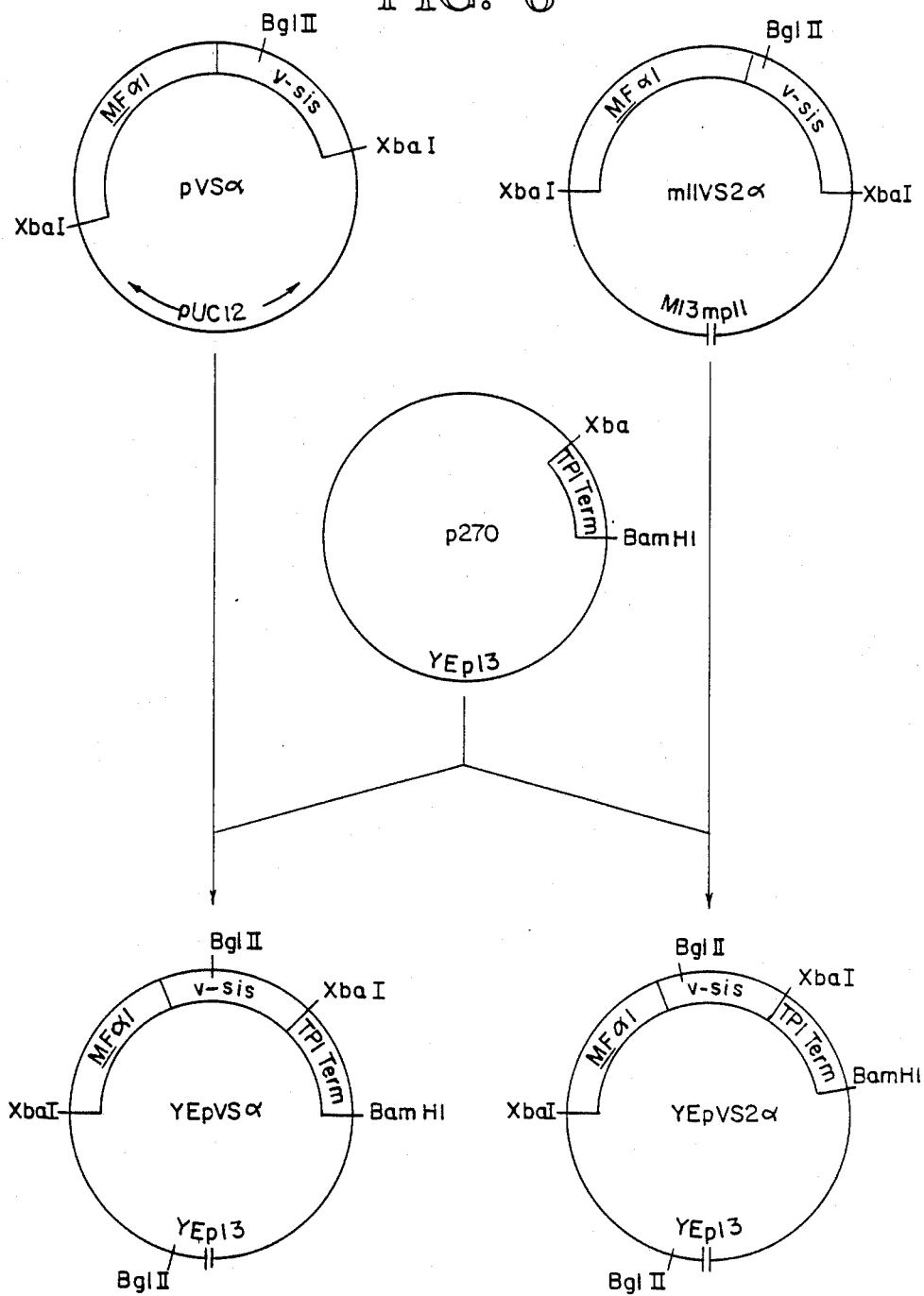
FIG. 6 illustrates the insertion of v-sis expression units upstream of the TPI terminator.

Referring to FIG. 6, plasmid p270 DNA was digested with Xba I and treated with calf alkaline phosphatase to prevent religation of the cohesive vector ends. V-sis expression units VS$\alpha$ and VS2$\alpha$ were prepared by Xba I digestion and agarose gel purification of pVS$\alpha$ and m11vs2$\alpha$, respectively. Each of the isolated fragments was ligated with an approximately equimolar amount of phosphatased p270 vector in the presence of 40 units of $T_4$ DNA ligase and the ligation mixtures transformed into *E. coli* K-12 RR1. Plasmid DNA was prepared from ampicillin-resistant colonies and restriction enzyme analysis performed in order to identify clones which possessed the TPI terminator adjacent to 3' v-sis sequences. Presence of 3.3 kb or 3.1 kb Bgl II fragments after gel electrophoresis indicated the correct orientation of YEpVS$\alpha$ and YEpVS2$\alpha$, respectively.

B. Insertion of VS2$\alpha$ Expression unit into pCPOT

In order to achieve maximal protein production from a yeast culture it is desirable to use expression vehicles which are very stably maintained in the host cell. Plasmid pCPOT is such a preferred expression vehicle. *E. coli* HB101 transformed with pCPOT has been deposited with American Type Culture Collection under accession number 39685. Plasmid pCPOT comprises the 2 micron circle genome (Hartley and Donelson, *Nature* 286: 860, 1980), *E. coli* plasmid pBR322 replication and selection sequences, and the *Schizosaccharomyces pombe* DNA sequences encoding the glycolytic enzyme Triose Phosphate Isomerase (POT1). Presence of the POT1 gene in pCPOT ensures stable maintenance of the plasmid in the appropriate host background during growth on nonselective medium utilizing glucose as a carbon source.

The *S. cerevisiae* TPI promoter was used to control expression of VS2$\alpha$ sequences in pCPOT. Plasmid pM220 contains the TPI promoter fused to the MF$\alpha$1 signal sequence. *E. coli* RRI transformed with pM220 has been deposited with American Type Culture Collection under accession number 39853.

Figure 7:
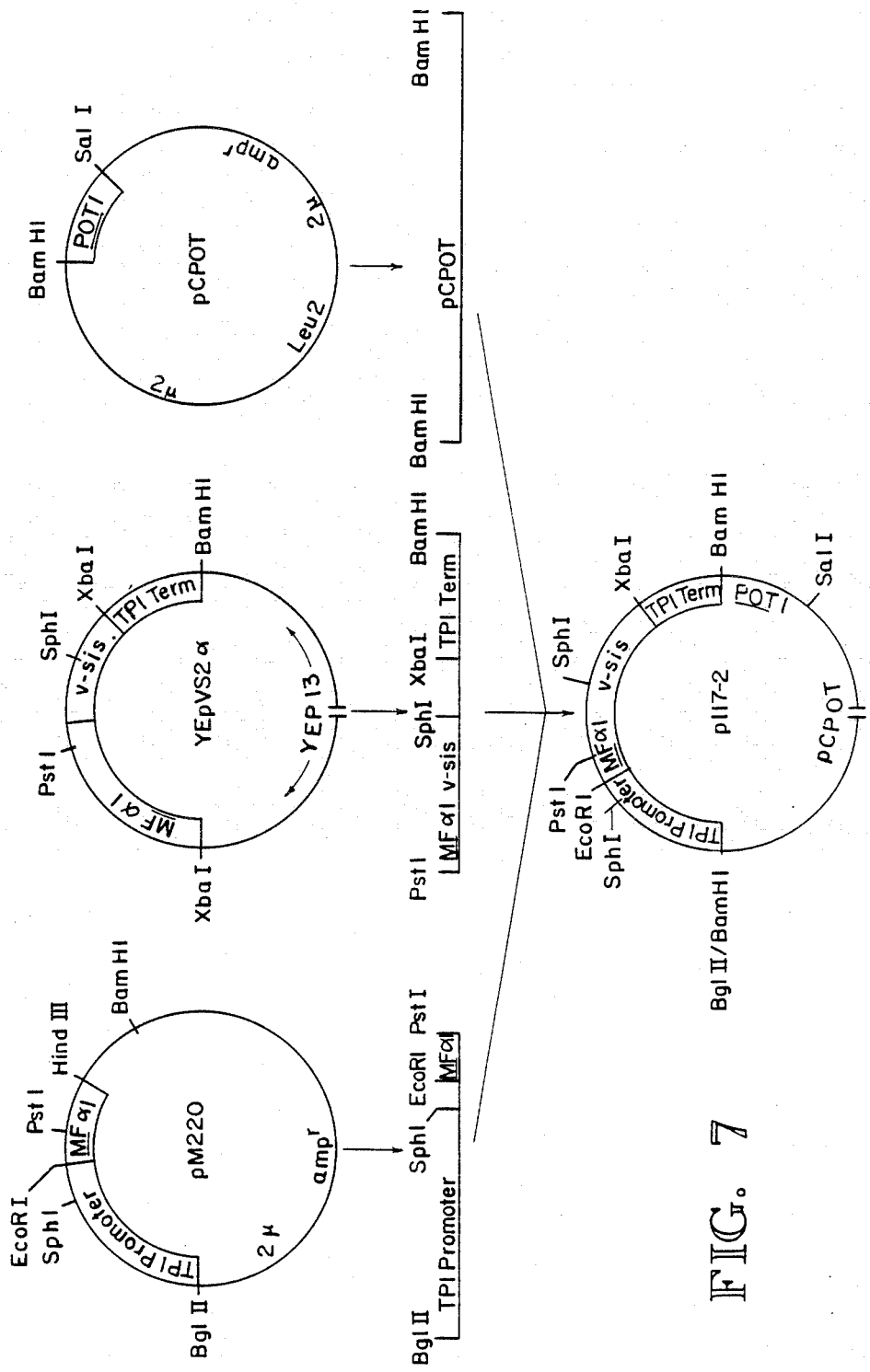
FIG. 7 illustrates the replacement of the MFα1 promoter with the TPI promoter and inclusion of the VS2α construction in the pCPOT vector.

Referring to FIG. 7, plasmid pM220 was digested with Bgl II and Bam HI, electrophoresed through a 0.9% agarose gel and the 2.2 kb TPI promoter, MF$\alpha$1 gene fragment extracted. The purified fragment was digested with Pst I and the resulting 1 kb Bgl II-Pst I fragment agarose gel purified as above. Plasmid YEpVS2$\alpha$ was digested with Pst I and Bam HI and the 1.8 kb MF$\alpha$1/v-sis/TPI terminator fusion fragment gel isolated. Plasmid pCPOT was digested with Bam HI, treated with calf alkaline phosphatase, phenol/CHCl$_3$ extracted, then purified by electrophoresis through agarose, extracted from the gel and ETOH precipitated.

Approximately equimolar amounts of the three isolated fragments described above (FIG. 7) were ligated overnight at 12° C. and the ligation mixture used to transform *E. coli* K-12 strain DH1 (Hanahan, D. and Meselson, M., *J. Mol. Biol.* 166: 557, 1983) to ampicillin resistance. Plasmid DNA was prepared from transformants and restriction digest analysis used to ascertain the orientation of the insert fragments. Presence of the ~1500 bp Bam HI-Sal I fragment indicates that the Bam HI cohesive end of the TPI terminator fragment is oriented as shown in FIG. 7. The opposite orientation would create a Bam HI/Bgl II fusion, not cleavable by Bam HI, and hence would not yield this fragment. The 800 bp Sph I fragment indicated that TPI promoter and v-sis fragments were properly fused at the Pst I site (FIG. 7). This plasmid was designated p117-2.

EXAMPLE V

Yeast Transformation; and Analysis of v-sis Transcription

*S. cerevisiae* strain E8-11c (MAT $\alpha$ leu2-3, 112 pep 4-3; a haploid segregant of the cross E2-7B [ATCC 20689]×GK 100 [ATCC 20669]) was transformed with plasmids YEpVS$\alpha$, YEpVS2$\alpha$, p270, p117-2 and pCPOT. Transformants were selected and maintained in synthetic medium lacking leucine.

*S. cerevisiae* strain E11-3c (deposited with ATCC, Accession # not assigned) (MAT $\alpha$ pep4-3 tpil), was transformed with plasmids pCPOT and p117-2. Transformants were selected and maintained in YEPD.

Figure 8:
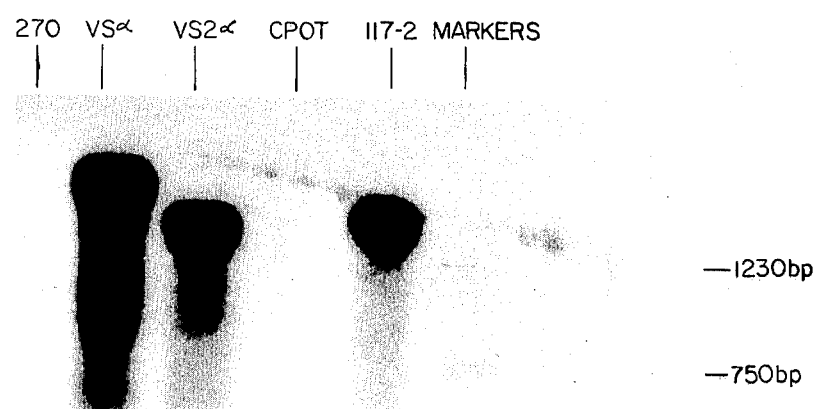
FIG. 8 depicts the electrophoretic and subsequently hybridization analysis of total RNA isolated from a yeast host transformed with various plasmids probed with a nick-translated v-sis gene fragment.

Referring to FIG. 8, presence of v-sis related mRNA transcripts was confirmed by electrophoretic and subsequent hybridization analysis of total RNA. Total RNA from the above described transformants in strain E8-11c was prepared by guanidinium thiocyanate extraction as described by Maniatis et al. (ibid.) with the following modifications: 100 ml cultures were grown to a density of $1 \times 10^8$ cells/ml. The cells were pelleted by centrifugation and washed three times with H$_2$O, 2 mls of guanidinium lysis solution was added, followed by 0.5 mm glass beads to just below the meniscus. The tubes were vortexed 3 times for 1 minute with cooling on ice between bursts. The solution was pipetted off and the RNA isolated by centrifugation through CsCl$_2$ as described (Maniatis et al., ibid.). Fifteen ug of RNA from plasmid transformants p270, YEpVS$\alpha$, YEpVS2$\alpha$, pCPOT and p117-2 was glyoxylated, electrophoresed through a 0.9% agarose gel and transferred to nitrocellulose as described by Thomas (*PNAS* 77: 5201, 1980). The purified Pst I v-sis fragment from pVSIS/Pst was nick translated and hybridized to the filter bound RNA, and the hybridizing species detected by autoradiography (FIG. 8). Transcript bands of ~1900 bp from YEpVS$\alpha$, ~1650 bp from YEpVS2$\alpha$, and ~1700 bp from p117-2 confirmed the transcription of the v-sis fusion constructs and the use of the transcription start and stop signals in the constructions. No v-sis related transcripts were detected in negative controls p270 and pCPOT.

EXAMPLE VI

Analysis of sis-related Products Expressed by Yeast; and Biological Activity Assays

A. Concentration of Yeast Culture Medium

Transformants carrying v-sis constructions were grown in the appropriate media at 30° C. (1.2 liter cultures) to stationary phase on a rotary air shaker with agitation at 220 rpm. Cultures were harvested, the cells removed by centrifugation, and the medium concentrated on a C-8 Sepharose (Pharmacia Fine Chemicals AB, Uppsala, Sweden) column which binds molecules of a hydrophobic nature. Authentic human PDGF is a highly cationic and hydrophobic protein (Heldin et al. PNAS 76: 3722, 1979; (Raines and Ross, ibid.). The sis-related putative yeast product was expected to possess similar characteristics. The sis products expected hydrophobic character was exploited to concentrate it from the yeast media into which it was expected to be secreted. Molecules bound to the C-8 column are eluted from the matrix with suitable hydrophobic solvents.

Spent growth media from the transformed yeast cultures was adjusted to 5% EtOH and passed through an 8 ml C-8 Sepharose column at a flow rate of 2-3 ml per minute. The column was then washed with 100 mls of 5% EtOH in 20 mM ammonium bicarbonate ($NH_4HCO_3$). The bound material was eluted with 20% propanol in 20 mM $NH_4HCO_3$ and the eluate collected in 1-2 ml fractions. Fractions were assayed for protein content by light absorption at 280 nm, ($A_{280}$ of 1.4=1.0 mg protein/ml) or by the method of Lowry et al. (J. Biol. Chem. 193: 165, 1951). The concentrated fractions were combined, lyophilized, and then resuspended in 500-700 ul of PBS (phosphate buffered saline, pH 7.4).

Transformant p117-2 in strain E11-3c grown under POT1 selection (with glucose as carbon source) was expected to produce significantly higher levels of PDGF-like material in the media and thus was analyzed after dialysis of the media against PBS without concentration.

B. Detection of PDGF-like Material By Enzyme-Linked Immunosorbent Assay (ELISA)

Figure 9:
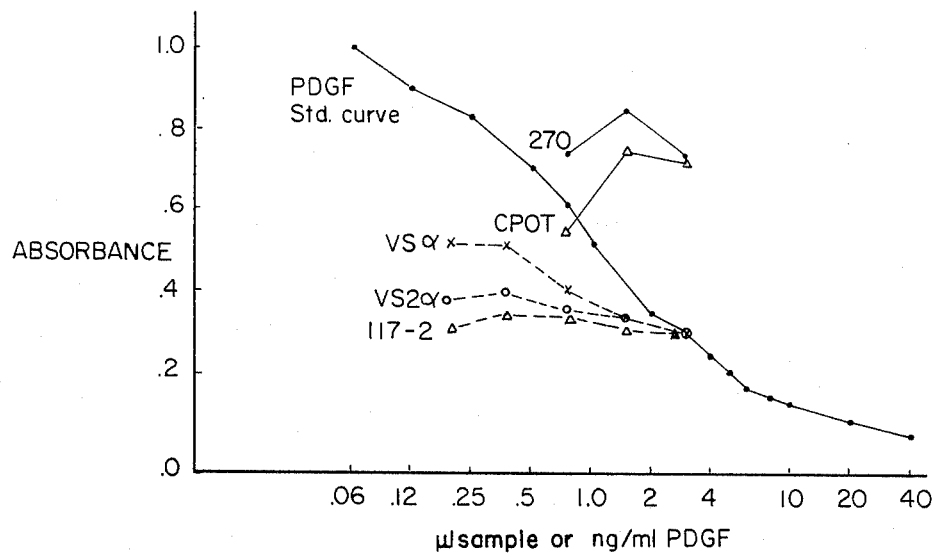
FIG. 9 depicts the results of ELISA of concentrated culture media from the yeast transformants.

The expression of PDGF-like molecules by the yeast transformants was examined by ELISA and quantitated by comparison to a standard curve developed with purified human PDGF (Raines and Ross, ibid.). A typical standard curve was prepared as follows:

Purified human PDGF, 2.5 ng/ml in PBS, was incubated overnight with Immulon II (Dynatech Laboratories, Inc.) 96 well microtiter plates (100 ul/well) at 4° C. This coating solution was removed and 100 ul/well of 0.1% rabbit albumin in PBS was added and the plates incubated for 1 hour at 37° C. Samples of purified PDGF (0.1-40 ng/ml) were separately incubated with goat anti-PDGF IgG (5 ug/ml) in PBS containing 0.05% Tween 20 and 1 mg/ml rabbit albumin (RSA). The microtiter plates were washed 5 times wih 0.9% NaCl, 0.05% Tween 20, drained, and 100 ul of each test solution was added to the microtiter wells and incubated 2 hours at 37° C. The plates were washed as before and freshly prepared 0.04% o-phenylene diamine containing 0.012% hydrogen peroxide ($H_2O_2$) (100 ul/well) was added for 50 minutes at room temperature and the reaction stopped at 50 minutes by the addition of 4N $H_2SO_4$ (50 ul/well). Absorbance at 492 nm was determined using a Dynatech plate scanner. Each test point was measured in triplicate and plotted as the mean±standard error. C-8 eluates of yeast culture media and unconcentrated media samples were diluted in PBS, assayed as described and compared to the PDGF standard curve. Table 1 is a summary of assay results for a representative series of experiments. FIG. 9 depicts an ELISA of a range of C-8 eluate sample volumes measured, generating a dose-response curve which is compared to a standard curve from purified PDGF.

C. Radioreceptor Assay (RRA) for PDGF

The radioreceptor assay for PDGF (Bowen-Pope and Ross, J. Biol. Chem. 257: 5161, 1982) is a specific and sensitive (0.2-2 ng/ml PDGF) method for detecting biologically active PDGF-like material in yeast. In this assay, PDGF-like material is tested for its ability to compete with purified, radio-labeled $^{125}I$ PDGF for binding sites on the cell surface PDGF receptors of Swiss mouse 3T3 cells. Results are interpreted by comparison to a standard curve generated with purified, unlabeled PDGF. Comparison of results obtained with other assay methods (e.g., ELISA) provides an indication of the strength of the receptor/ligand interaction in addition to quantitation of the material bound. The assay is conducted as follows: Subconfluent monolayers of diploid human fibroblasts are prepared by plating $1.5 \times 10^4$ cells per 2 $cm^2$ culture well in Costar 24 well cluster trays in Dulbeccos Modified Eagles Medium (DMEM) supplemented with 1% human plasma-derived serum (PDS). Cultures are set on an ice tray and rinsed once with ice-cold binding rinse (Ham's medium F-12 buffered at pH 7.4 with 25 mM HEPES and supplemented with 0.25% BSA). One ml/well of test substance in binding medium is added and the cultures incubated in a refrigerated room on an oscillating platform for 3-4 hours. The trays are then placed on ice, aspirated, rinsed once with cold binding rinse and incubated for one hour as above with 1 ml/well binding medium containing 0.5 ng/ml $^{125}I$-PDGF. Labeling is terminated with 4 rinses of binding rinse and cell-associated $^{125}I$-PDGF determined by extraction with solubilization buffer. Standard curves are obtained using 0, 0.05, 0.1, 0.2, 0.4, and 0.8 ng/ml purified PDGF and test samples compared to these values.

Results obtained by RRA for yeast C-8 eluates and 1X media samples are given in Table 1.

D. Mitogenesis Assay

The ability of PDGF to stimulate DNA synthesis and cell growth in culture was the basis for its definition and discovery. $^3H$-Thymidine incorporation into DNA of cultured cells responsive to PDGF (Raines and Ross, Meth. in Enz. 109: in press) is a preferred method for demonstrating the biological activity of PDGF-like molecules produced in yeast.

Test samples in 10 mM acetic acid (100 ul/well) are added to quiescent cultures of mouse 3T3 cells in 2 $cm^2$ Costar 24-well culture dishes ($2-3 \times 10^8$ cells/well in 1 ml). Quiescent test cultures can be obtained by plating the cells in 10% serum and allowing them to deplete the medium, 4-5 days. The test samples are removed from the wells at 20 hours and replaced with 0.5 ml of fresh medium per well containing 2 uCi/ml [$^3H$]-Thymidine and 5% (v/v) calf serum. After an additional 2-hour incubation at 37° C. the cells are harvested by: aspirating off the medium, washing the wells twice each with 1 ml of ice-cold 5% TCA; solublizing TCA-insoluble material in 0.8 ml 0.25N NaOH with mixing; and counting 0.6 ml of this solution in 5 ml Aquasol in a liquid scintillation counter. Fold stimulation over control wells (100 ul of 10 mM acetic acid alone) is determined, (normally 30-50 fold maximal stimulation) and compared to a standard curve obtained using purified PDGF preparations.

Figure 10:
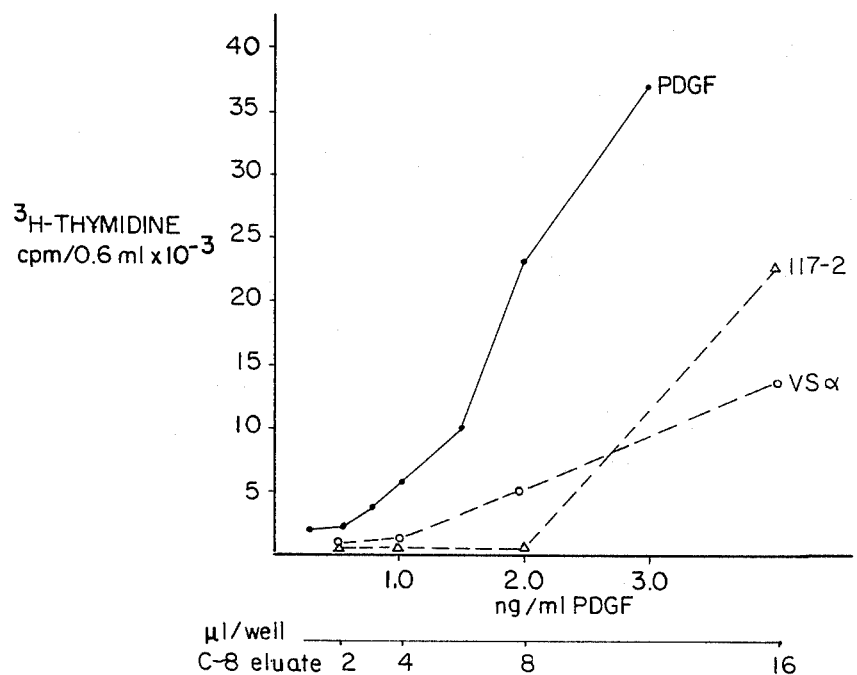
FIG. 10 is a dose response curve of mitogenic activity of concentrated culture media from the yeast transformants compared to purified PDGF.

Table 1 presents results obtained in the mitogenesis assay for PDGF-like material produced in yeast and compares the activities of the PDGF-like material as measured by the above described assay methods. FIG. 10 depicts the mitogenic response illicited by concentrated media from p117-2 transformed E11-3c and pVSα transformed E8-11c compared to that obtained with purified human PDGF.

TABLE 1

| Preparation | Transformant | ug/ml Protein | ng/ml PDGF by | | |
|---|---|---|---|---|---|
| | | | ELISA | RRA | MITO-GEN-ESIS |
| C-8 Eluates | pVSα/E8-11c | 2.0 | 188 | 4.6 | 102 |
| | pVS2α/E8-11c | 16 | 864 | 16-97 | 310 |
| | p117-2/E11-3c | 1.44 | 120 | 13.9 | 87 |
| 1X Media | p117-2 E11-3c | — | 4.2 | 0.18 | 2.5 |

The data present clear evidence that growth media from the yeast strains constructed herein possess biological activities identical to authentic human PDGF. Further, these activities are readily detectable in nonconcentrated (1X) media from p117-2 transformed strain E11-3c grown under POT1 selection.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A vector capable of replication in yeast and containing a yeast promoter capable of directing the expression of biologically active PDGF analogs, said yeast promoter being followed downstream by a gene encoding a protein having substantially the same biological activity as PDGF.

2. The vector of claim 1 wherein said promoter is the yeast alpha-factor promoter or the yeast triose phosphate isomerase promoter.

3. The vector of claim 1 wherein said promoter is followed downstream by the signal sequence of the yeast mating pheromone alpha-factor.

4. The vector of claim 1 wherein said gene is the v-sis gene of simian sarcoma virus or portions thereof.

5. The vector of claim 1 wherein said gene is a derivative of the v-sis gene of simian sarcoma virus or portions thereof.

6. The vector of claim 1 wherein said gene is the human cDNA gene for PDGF or portions thereof.

7. The vector of claim 1 wherein said gene is followed downstream by a triose phosphate isomerase terminator.

8. The vector of claim 6 wherein said human gene is derived from mRNA isolated from endothelial cells.

9. The vector of claim 1 wherein said protein is a disulfide-bonded dimeric protein.

10. A vector capable of replication in yeast and containing the yeast triose phosphate isomerase promoter, said yeast promoter being followed downstream by the signal sequence of the yeast mating pheromone alpha-factor, said signal sequence being followed downstream respectively by the portion of the v-sis gene encoding a polypeptide which is substantially homologous to the B chain of PDGF, and a triose phosphate isomerase terminator.

11. A method of preparing biologically active PDGF analogs, comprising:
   introducing into a yeast host a vector capable of replication in yeast and containing a yeast promoter capable of directing the expression of biologically active PDGF analogs, said yeast promoter being followed downstream by a gene encoding a protein having substantially the same biological activity as PDGF;
   growing said yeast host in an appropriate medium; and
   isolating the protein product of said gene from said yeast host.

12. The method of claim 11 wherein said promoter is the yeast alpha-factor promoter or the yeast triose phosphate isomerase promoter.

13. The method of claim 12 wherein said promoter is followed downstream by the signal sequence of the yeast mating pheromone alpha-factor.

14. The method of claim 13 wherein said gene is the v-sis gene of simian sarcoma virus or portions thereof.

15. The method of claim 14 wherein said gene is a derivative of the v-sis gene of simian sarcoma virus or portions thereof.

16. The method of claim 15 wherein said gene is the human cDNA gene for PDGF or portions thereof.

17. The method of claim 16 wherein said human gene is derived from mRNA isolated from endothelial cells.

18. The method of claim 17 wherein said gene is followed downstream by a triose phosphate isomerase terminator.

19. The method of claim 11, including after isolation of said protein product, purifying said product by gel filtration, ion exchange chromatography of affinity chromatography.

20. The method of claim 19 wherein said medium need not contain antibiotics or heavy metals, and need not be depleted of specific nutrients.

21. The method of claim 19 wherein said protein is a disulfide-bonded dimeric protein.

22. A yeast cell transformed with a vector capable of replication in yeast and containing a yeast promoter capable of directing the expression of biologically active PDGF analogs, said yeast promoter being followed downstream by a gene encoding a protein having substantially the same biological activity as PDGF.

23. The yeast cell of claim 22 wherein said promoter is the yeast alpha-factor promoter or the yeast triose phosphate isomerase promoter.

24. The yeast cell of claim 23 wherein said promoter is followed downstream by the signal sequence of the yeast mating pheromone alpha-factor.

25. The yeast cell of claim 24 wherein said gene is the v-sis gene of simian sarcoma virus or portions thereof.

26. The yeast cell of claim 25 wherein said gene is a derivative of the v-sis gene of simian sarcoma virus or portions thereof.

27. The yeast cell of claim 26 wherein said gene is the human cDNA gene for PDGF or portions thereof.

28. The yeast cell of claim 27 wherein said human gene is derived from mRNA isolated from endothelial cells.

29. The yeast cell of claim 28 wherein said protein is a disulfide-bonded dimeric protein.

30. The yeast cell of claim 29 wherein said vector is the plasmid p117-2.

31. The yeast cell of claim 30 wherein said vector is the plasmid YEpVSα.

32. The yeast cell of claim 31 wherein said vector is the plasmid YEpVS2α.

33. The yeast cell of claim 32 wherein said gene is followed downstream by a triose phosphate isomerase terminator.

34. A method of promoting the growth of mammalian cells, comprising incubating the cells with a biologically active PDGF analog expressed by a yeast cell transformed with a vector capable of replication in yeast said vector containing a yeast promoter capable of directing the expression of the PDGF analog, said yeast promoter being followed downstream by a gene encoding a protein having substantially the same biological activity as PDGF.

35. The method of claim 34 wherein said growth is carried out in vitro.

36. The method of claim 34 wherein said cells are normal cells or transformed cells.

37. The method of claim 34 wherein said protein is a disulfide-bonded dimeric protein.

38. The plasmid p117-2.

39. The plasmid YEpVSα.

40. The plasmid YEpVS2α.

41. A vector capable of replication in yeast and containing the yeast triose phosphate isomerase promoter, said yeast promoter being followed downstream by the signal sequence of the yeast mating pheromone alpha-factor, said signal sequence being followed downstream respectively by the v-sis gene of simian sarcoma virus or portions thereof encoding a protein having substantially the same biological activity as PDGF, and a triose phosphate isomerase terminator.

42. The vector of claim 13 wherein said protein is a disulfide-bonded dimeric protein.

43. A vector capable of replication in yeast and containing a yeast promoter capable of directing the expression of biologically active PDGF analogs, said yeast promoter being followed downstream by the portion of the v-sis gene encoding a polypeptide which is substantially homologous to the B chain of PDGF, said portion encoding a protein having substantially the same biological activity as PDGF.

44. The vector of claim 15 wherein said protein is a disulfide-bonded dimeric protein.

45. A method of preparing biologically active PDGF analogs, comprising:

introducing into a yeast host a vector capable of replication in yeast and containing a yeast promoter capable of directing the expression of biologically active PDGF analogs, said yeast promoter being followed downstream by the portion of the v-sis gene encoding a polypeptide which is substantially homologous to the B chain of PDGF, said portion encoding a protein having substantially the same biological activity as PDGF;

growing said yeast host in an appropriate medium; and isolating the protein product of said gene from said yeast host.

46. The method of claim 32 wherein said protein is a disulfide-bonded dimeric protein.

47. A yeast cell transformed with a vector capable of replication in yeast and containing a yeast promoter capable of directing the expression of biologically active PDGF analogs, said yeast promoter being followed downstream by the portion of the v-sis gene encoding a polypeptide which is substantially homologous to the B chain of PDGF, said portion encoding a protein having substantially the same biological activity as PDGF.

48. The yeast cell of claim 10 wherein said protein is a disulfide-bonded dimeric protein.

* * * * *